United States Patent [19]

Garlick

[11] Patent Number: 4,656,280

[45] Date of Patent: Apr. 7, 1987

[54] RADIOIODINATED DOPAMINE RECEPTOR LIGAND

[75] Inventor: Russell K. Garlick, Townsend, Mass.

[73] Assignee: E. I. Du Pont de Nemours and Company, Wilmington, Del.

[21] Appl. No.: 587,061

[22] Filed: Mar. 7, 1984

[51] Int. Cl.$^4$ .................. C07D 471/10; C09K 11/04; G01N 33/567

[52] U.S. Cl. .................... 546/20; 252/645; 424/1.1; 424/9; 436/504

[58] Field of Search ............ 546/20; 424/1.1, 9; 252/645; 549/29, 75; 436/504

[56] References Cited

U.S. PATENT DOCUMENTS

| | | | |
|---|---|---|---|
| 3,897,212 | 7/1975 | Leon et al. | 436/542 |
| 4,305,944 | 12/1981 | Temple, Jr. et al. | 424/250 |
| 4,411,881 | 10/1983 | Tzodikov | 424/1.1 |
| 4,411,901 | 10/1983 | Temple, Jr. et al. | 424/250 |
| 4,452,799 | 6/1984 | Temple, Jr. et al. | 424/250 |

OTHER PUBLICATIONS

Srinivasta, P. C. et al., J. Heterocyclic Chim. vol. 20, pp. 1081–1084, (7-1983).
Tejedor, F. et al., Analytical Biochemistry, vol. 128, pp. 115–120, (1-1983).
Kulkarni, P. V. et al., J. Nuclear Medicine, vol. 23(5), p. p105, (6-1982).
Chan, H. C. et al., Biochemistry, vol. 15, pp. 5487–5490, (1976).
Anderson, D. M. et al., Biochemistry, vol. 15(5), pp. 1022–1030, (1976).
Schmidt, F. J. et al., Biochemistry, vol. 12(24), pp. 4980–4983, (1973).
Gundlach, A. L. et al., Life Sciences, vol. 35, pp. 1981–1988, (1984).
Pogun, S. et al., Nucl. Med. Biol. Adv. Proc. World Congr. 3rd Meeting Date 1982, vol. 4, pp. 3606–3609, Raynaud, C. ed, Pergamon, Oxford, U.K. (1983), CA 98(21): 175663u.
Lu, D. et al., Nucl. Tech., vol. (3), pp. 51–52, (1983).
Commerford, S. L., Biochemistry, vol. 10(11), pp. 1993–1999, (1971).
Kulmala, H. K. et al., Life Sci., vol. 28(17), pp. 1911–1916, (1981), CA 95:57281h.
Owen, F. et al., Life Sci., vol. 33(8), pp. 765–768, (1983), CA 99(15):116264n.
DeJesus, O. T. et al., J. Labelled Compd. Radiopharm., vol. 20(6), pp. 745–756, (1983), CA 99(25):212407g.
Friedman, A. M. et al., Ann. Nevrol., vol. 15, pp. 66–76, (1984), CA 101(7): 48726x.
Barrio, J. R. et al., J. Chem. Soc., Chem. Commun., vol. (8), pp. 443–444, (1983), ($^{18}$F).
Van Parys, M. et al., Bull. Soc. Chem. Belg., vol. 90, pp. 749–755, (1981).

*Primary Examiner*—Charles F. Warren
*Assistant Examiner*—M. Moskowitz

[57] ABSTRACT

A process for the production of radioiodinated spiperone and certain derivatives thereof, and novel compositions made by the process. The process includes reacting spiperone, thallium trichloride and radioiodine in a sealed reaction vial. The novel compounds are useful for diagnosis of disease states resulting in quantitative changes in dopaminergic receptors.

7 Claims, No Drawings

RADIOIODINATED DOPAMINE RECEPTOR LIGAND

BACKGROUND

The subject invention relates to radiolabeling dopamine receptor ligands. More specifically, the subject invention relates to radioiodination of the dopamine receptor ligand generally known as spiperone, and certain derivatives thereof.

It has been known for some time that spiperone is an antagonist of the dopamine receptor. Further, tritiated spiperone has long been used as a research tool for the characterization and quantitation of dopamine receptors, particularly in the study of certain disease states which result in quantitative changes in dopaminergic receptors such as Parkinson's and Huntington's diseases, and schizophrenia. Tritium, however, is a weak beta emitter which requires quantitation by liquid scintillation counting. Tritium is also a low specific activity isotope, therefore assays being tritiated spiperone require inconveniently large amounts of tissue.

Radiobrominated spiperone has also been prepared for use in vitro to test dopamine receptor binding affinity, and in vivo to image dopamine receptors and to study stimulation of prolactin secretion. Use of radiobrominated spiperone, however, suffers from the disadvantage of having a very short half-life (57 hours). Also, Br-77 is not commercially available.

Preparation of non-radioactive iodinated spiperone has also been reported. However, this non-radioactive iodinated spiperone was reported to have a twenty-fold decrease in dopamine receptor binding affinity. Also, the process used for this iodination is unknown.

SUMMARY

The subject invention is a process for the production of radioiodinated ($^{123}$I, $^{125}$I, $^{129}$I, $^{131}$I) spiperone and certain derivatives thereof, and the novel compositions made by the process. These compounds are useful for diagnosis of disease states which result in quantitative changes in dopaminergic receptors, and are useful in the detection, isolation and characterization of dopamine receptors. The compounds exhibit a 100-fold increase in specific activity over the tritiated counterparts, and because they are gamma emitters, allow for easier handling and counting.

DETAILED DESCRIPTION

The subject invention is useful for the preparation of radioiodinated forms of the 4-phenyl compounds described in U.S. Pat. Nos. 3,155,669; 3,155,670 and 3,161,644 issued to Janssen and incorporated herein by reference.

The nomenclature employed below is based on the following nucleus:

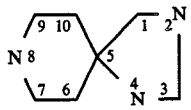

The compounds to be radioiodinated using the process of the subject invention are pharmacologically active substances of the general formula 1-oxo-2-$R_1$-3-$R_2$-4-$R_3$-8-$R_4$-triaza-spiro(4,5)-decane where $R_1$ and $R_2$ are preferably hydrogen but can be lower alkyl (one C to three C); $R_3$ is phenyl (unsubstituted or substituted as detailed below); and $R_4$ is $Z(CH_2)n$ where n is a positive integer from 0 to 4, and Z is any of a variety of groups as illustrated below and disclosed in the aforementioned U.S. patents issued to Janssen. The following compounds are representative:

1-oxo-4-phenyl-8-[3-(4-fluorobenzoyl)-propyl]-2,4,8-triaza-spiro(4,5)decane.
1-oxo-4-phenyl-8-(3-benzoylpropyl)-2,4,8-triaza-spiro(4,5)decane
1-oxo-4-phenyl-8-[4-oxo-4-(2-thienyl)-butyl]-2,4,8-triaza-spiro(4,5)decane.
dl-1-oxo-3-methyl-4-phenyl-8-[3-(4-fluorobenzoyl)-propyl]-2,4,8-triaza-spiro(4,5)decane.
1-oxo-4-phenyl-2-acetyl-8-[3-(4-fluorobenzoyl)-propyl]-2,4,8-triaza-spiro(4,5)decane hydrochloride.
1-oxo-4-phenyl-8-[3-(4-chlorobenzoyl)-propyl]-2,4,8-triaza-spiro(4,5)decane.
1-oxo-4-phenyl-8-[2-(1,4-benzodioxanyl)-methyl]-2,4,8-triaza-spiro(4,5)decane
1-oxo-4-phenyl-8-benzyl-2,4,8-triaza-spiro(4,5)decane.
1-oxo-4-phenyl-8-(4-methylbenzyl)-2,4,8-triaza-spiro(4,5)decane.
1-oxo-2-methyl-4-phenyl-8-benzyl-2,4,8-triaza-spiro(4,5)decane.
1-oxo-4-phenyl-8-(3-cyano-3,3-diphenylpropyl)-2,4,8-triaza-spiro(4,5)decane.
1-oxo-2-(hydroxymethyl)-4-phenyl-8-benzyl-2,4,8-triaza-spiro(4,5)decane
1-oxo-4-phenyl-8-(2-methylbenzyl)-2,4,8-triaza-spiro(4,5)decane.
1-oxo-4-phenyl-8-(4-fluorobenzyl)-2,4,8-triaza-spiro(4,5)decane.
1-oxo-2-methyl-4-phenyl-8-[3-(4-fluorobenzoyl)-propyl]-2,4,8-triaza-spiro(4,5)decane hydrochloride.

Most preferred are compositions of the formula

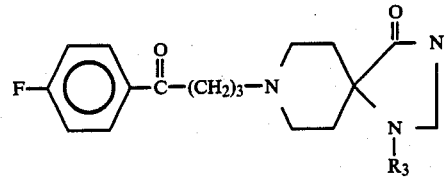

where $R_3$ is

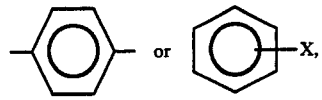

and X is selected from the group consisting of $NH_2$, OH, $NHR_5$ or $N(R_6)_2$ (where $R_5$ and $R_6$ are lower alkyl), $N_3$, $NHCOCH_3$ or $OCH_3$.

Where X in the formula above is $N_3$, the compounds are useful as photo-affinity ligands in a well-known technique for irreversibly binding receptor ligands to their respective receptor sites.

RADIOIODINATION

The radioiodination of spiperone (including derivatives thereof as herein described) is a one step synthesis whereby spiperone (in any standard solvent such as ethanol), thallium trichloride (dissolved in $H_2O$, $NaH_2PO_4$ buffers etc.) and radioiodine (in solution such as 0.1M NaOH) are allowed to react in a sealed reaction vial. The radioiodine is preferably carrier-free, but can be less than carrier-free. Any of the well known radioisotopes of iodine may be used, e.g. I-123, I-125, I-129 and I-131.

The reaction is carried out under acidic conditions (pH about 1-6), in an aqueous buffer at about 50°-80° C. for 10-60 minutes.

The resulting compound may then be purified by conventional reverse phase HPLC, normal phase HPLC, TLC or by chromatographic methods such as open column silica gel and alumina. The compound is preferably stored in a solution containing free radical scavengers such as ethanol, propanol or buffers containing proteins.

These novel radioiodinated compounds are radioiodinated on the 4-phenyl ring in the para position where the ring is unsubstituted, and in the meta position when the ring is substituted in the para position.

Therefore, the radioiodinated counterparts of the compounds above are as defined where $R_3$ is

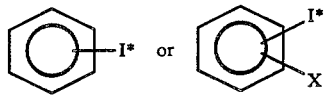

where I* is radioiodine and X is selected from the group consisting of OH, $NH_2$, $NHR_5$ or $N(R_6)_2$ (where $R_5$ and $R_6$ are lower alkyl), $N_3$, $OCH_3$, or $NHCOCH_3$.

The following example illustrates the preferred embodiment of the invention.

EXAMPLE

This example illustrates the preparation of:
1-oxo-4-(p-iodo-phenyl)-8-[3-(4-fluorobenzoyl)-propyl]-2,4,8-triaza-spiro(4,5)decane,($^{125}$I)

The following ingredients are added to a sealable reaction vial (variations of ±10% of each reagent are acceptable):
(i) 10 mCi carrier-free $^{125}$I ($4.5 \times 10^{-9}$ Moles) in 0.1M NaOH.
(ii) spiperone (1-oxo-4-phenyl-8-[3-(4-fluorobenzyl)-propyl]-2,4,8-triaza spiro(4,5)decane) ($1.06 \times 10^{-7}$ Moles) in ethanol (42 μl)
(iii) $NaH_2PO_4$ (0.9 ml, 0.5M, pH 4.5)
(iv) thallium trichloride (0.006 ml, $9 \times 10^{-8}$ moles in water)

and heated to 65° C. and allowed to react for about 20 minutes. The resulting solution is purified by HPLC using a reverse phase column such as a "μ-Bondapack" C-18 from Waters Associates, eluted with an organic/aqueous buffer (methanol: triethyl ammonium phosphate, 0.01M, pH 2.7. Upon analysis by HPLC and TLC it is determined that about 90% of original radioactivity is incorporated. Also, the affinity of the ligand for the dopamine receptor is maintained at about 3 nanomolar as determined in a receptor binding assay using rat striatum tissue.

I claim:

1. A process for the manufacture of a radioiodinated dopamine receptor ligand comprising admixing
   (i) a compound of the formula 1-oxo-2-$R_1$-3-$R_2$-4-$R_3$-8-$R_4$-triaza spiro(4,5)decane where $R_1$ and $R_2$ are hydrogen or lower alkyl; $R_4$ is $Z(CH_2)n$ where n is a positive integer from 0 to 4, Z is selected from 3-(4-fluorobenzoyl); 3-benzoyl; 4-oxo-4-(2-thienyl); 3-(4-chlorobenzoyl); 2-(1,4-benzodioxanyl); benzyl; 4-methyl-benzyl; 3-cyano-3,3-diphenyl; 2-methylbenzyl; and 4-fluorobenzyl; and where $R_3$ is

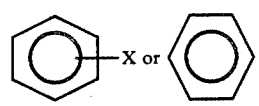

where X is a member of the group consisting of OH, $NH_2$, $NHR_5$ or $N(R_6)_2$ (where $R_5$ and $R_6$ are lower alkyl), $N_3$, $NHCOCH_3$ and $OCH_3$;
   (ii) thallium tri-chloride; and
   (iii) a substantially carrier-free radioisotope of iodine at a temperature and for a time sufficient to allow formation of the radioiodinated form of (i).

2. The process of claim 1 where (i) is 1-oxo-4-phenyl-8-[3-(4-fluorobenzoyl)-propyl]-2,4,8-triazo-spiro(4,5)-decane.

3. The process of claim 1 or 2 wherein $R_3$ is

4. The process of claim 1 or 2 where $R_3$ is

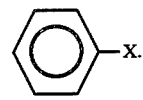

5. The process of claim 1 or 2 wherein the pH of the admixture is between about 1 and 6.

6. A radioiodinated dopamine receptor ligand produced by the process of claim 1 which has substantially all dopamine receptor binding activity retained.

7. A dopamine receptor ligand produced by the process of claim 2 which has substantially all dopamine receptor binding activity retained.

* * * * *